(12) United States Patent
Jaehne et al.

(10) Patent No.: US 7,772,429 B2
(45) Date of Patent: Aug. 10, 2010

(54) DIPHENYLAZETIDINONE WITH IMPROVED PHYSIOLOGICAL PROPERTIES, PROCESS FOR ITS PREPARATION, MEDICAMENTS COMPRISING THIS COMPOUND, AND ITS USE

(75) Inventors: Gerhard Jaehne, Frankfurt (DE); Wendelin Frick, Hunstetten-Beuerbach (DE); Andreas Lindenschmidt, Bad Soden (DE); Stefanie Flohr, Basel (CH); Hubert Heuer, Schwabenheim (DE); Hans-Ludwig Schaefer, Hochheim (DE); Werner Kramer, Mainz-Laubenheim (DE); Eric Galia, Frankfurt (DE); Heiner Glombik, Hofheim (DE)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 806 days.

(21) Appl. No.: 11/690,993

(22) Filed: Mar. 26, 2007

(65) Prior Publication Data
US 2007/0197498 A1    Aug. 23, 2007

Related U.S. Application Data

(63) Continuation of application No. 10/813,954, filed on Mar. 31, 2004, now Pat. No. 7,205,290.

(30) Foreign Application Priority Data

Apr. 1, 2003    (DE) ............................. 103 14 610

(51) Int. Cl.
*C07C 229/08*    (2006.01)
*C07C 229/12*    (2006.01)
(52) U.S. Cl. ..................................... 562/567
(58) Field of Classification Search ........................ None
See application file for complete search history.

(56) References Cited

U.S. PATENT DOCUMENTS

| | | | |
|---|---|---|---|
| 5,756,470 | A | 5/1998 | Yumibe et al. |
| 6,221,633 | B1 | 4/2001 | Ertl |
| 6,221,897 | B1 | 4/2001 | Frick |
| 6,245,744 | B1 | 6/2001 | Frick |
| 6,342,512 | B1 | 1/2002 | Kirsch |
| 6,624,185 | B2 | 9/2003 | Glombik |
| 6,884,812 | B2 | 4/2005 | Glombik |
| 6,992,067 | B2 * | 1/2006 | Glombik et al. ............... 514/23 |
| 7,176,194 | B2 | 2/2007 | Jaehne |
| 7,470,678 | B2 | 12/2008 | Starke et al. |

FOREIGN PATENT DOCUMENTS

| | | |
|---|---|---|
| EP | 0462884 | 6/1993 |
| EP | 0 656 354 | 6/1997 |
| WO | WO 97/26265 | 7/1997 |
| WO | WO 98/08871 | 3/1998 |
| WO | WO 99/03861 | 1/1999 |
| WO | WO 99/15525 | 4/1999 |
| WO | WO 99/46262 | 9/1999 |
| WO | WO 00/34331 | 6/2000 |
| WO | WO 00/40569 | 7/2000 |
| WO | WO 00/64876 | 11/2000 |
| WO | WO 00/64888 | 11/2000 |
| WO | WO 00/71549 | 11/2000 |
| WO | WO 00/78312 | 12/2000 |
| WO | WO 01/04156 | 1/2001 |
| WO | WO 01/09111 | 2/2001 |
| WO | WO 01/62266 | 8/2001 |
| WO | WO 01/83451 | 11/2001 |
| WO | WO 01/85695 | 11/2001 |
| WO | WO 01/90094 | 11/2001 |
| WO | WO 02/44150 | 6/2002 |
| WO | WO 02/50027 | 6/2002 |
| WO | WO 03/015769 | 2/2003 |

OTHER PUBLICATIONS

Asakawa A. et al., Cocaine-Amphetamine-Regulated Transcript Influences Energy Metabolism, Anxiety and Gastic Emptying in Mice, Hormone and Metabolic Research, (2001) vol. 33, No. 9, pp. 554-558.
Barf Tjeerd et al., Arylsulfonamidothiazoles as a New Class of Potential Antidiabetic Drugs. Discovery of Potent and Selective Inhibitors of the 11 Beta-Hydroxysteroid Dehydrogenase Type 1, American Chemical Society, (2002), vol. 45, No. 18, pp. 3813-3815.
Ishihara Kazuaki et al., 3,4,5-Trifluorobenzeneboronic Acid as an Extremely Active Amidation Catalyst, J. Org. Chem., (1996), vol. 61, pp. 4196-4197.
Klausner Yakir S. et al., Coupling Reagents in Peptide Synthesis, Sep. 1972.

(Continued)

*Primary Examiner*—Daniel M Sullivan
*Assistant Examiner*—Yevegeny Valenrod
(74) *Attorney, Agent, or Firm*—Barbara E. Kurys

(57) ABSTRACT

The invention relates to the compound of the formula 1

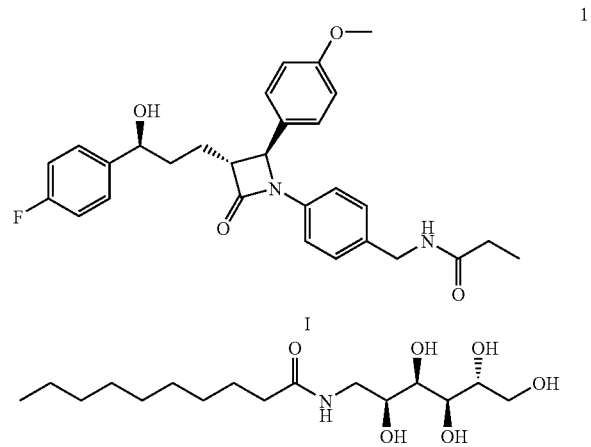

and to its physiologically acceptable salts. The compound is suitable, for example, as a hypolipidemic.

1 Claim, No Drawings

OTHER PUBLICATIONS

Kunishima Munetaka et al., 4-(4,6-Dimethoxy-1,3,5-triazin-2-yl)-4-methyl-morpholinium Chloride: An Efficient Condensing Agent Leading to the Formation of Amides and Esters, Tetrahedron, (1999), vol. 55, pp. 13159-13170.

Larock, R.C., Interconversion of Nitriles, Carboxylic Acids and Derivatives, Comprehensive Organic Transformations: A Guide to Functional Group Preparations, VCH Publishers, New York, Weinheim; 1999; pp. 1929-1930.

Lee Daniel W. et al., Leptin Agonists as a Potential Approach to the Treatment of Obesity, Drugs of the Future, (2001), vol. 26, No. 9, pp. 873-881.

Okada H. et al., Synthesis and Antitumor Activities of Prodrugs of Benzoylphenylureas, Chem. Pharm. Bull., (1994), vol. 42, No. 1, pp. 57-61.

Salvador Javier et al., Perspectives in The Therapeutic Use Of Leptin, Expert Opinion Pharmacotherapy, (2001), vol. 2, No. 10, pp. 1615-1622.

Speicher A. et al., O-(1-Benzotriazoly1)-N,N,N,N,-tetramethyluroniumhexafluorophosphat (HBTU) und O-(7-Aza-1-benzotriazolyl)-N,N,N,N -tetramethyluroniumhexafluorophosphat (HATU) -zwei moderne Kupplungsreagenzien zur Peptidsynthese, J. prakt. Chem., (1998), vol. 340, pp. 581-583.

Zunfit H. J. F. et al., Carob Pulp Preparation for Treatment of Hypercholesterolemia, Advances in Therapy, (2001), vol. 18, No. 5, pp. 230-236.

* cited by examiner

DIPHENYLAZETIDINONE WITH IMPROVED PHYSIOLOGICAL PROPERTIES, PROCESS FOR ITS PREPARATION, MEDICAMENTS COMPRISING THIS COMPOUND, AND ITS USE

This application is a continuation of application Ser. No. 10/813,954, filed Mar. 31, 2004, now U.S. Pat. No. 7,205,290.

The invention relates to a substituted diphenylazetidinone, to its physiologically acceptable salts and to physiologically functional derivatives.

Diphenylazetidinones and their use for treating hyperlipidemia and also arteriosclerosis and hypercholesterolemia have already been described (WO 02/50027).

It was an object of the invention to provide a compound which, compared to the compounds described in WO 02/50027, has considerably better solubility in the upper small intestine in the pre- and/or postprandial state. The improved solubility of the compound ensures higher availability of dissolved substance at the site of action and thus improved efficacy.

FaSSIF (fasted State Simulating Intestinal Fluid) and FeSSIF (Fed State Simulating Intestinal Fluid) media which reflect the pH/solubilization conditions in the upper small intestine in the pre- and postprandial state, respectively, were used to test this improved solubility.

It was another object of the invention to provide a compound which, compared to the compounds described in WO 02/50027, has increased stability both in the acidic range (stomach) and in the weakly alkaline range (small intestine). This property leads to fewer byproducts/cleavage products which for their part may have unwanted side-effects. However, increased stability in the acidic range is also a great advantage for formulation since in this case there is no need for an acid-resistant capsule/tablet.

Accordingly, the invention relates to the compounds of the formula I fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium salts and potassium salts), alkaline earth metal salts (such as magnesium salts and calcium salts), trometamol (2-amino-2-hydroxymethyl-1,3-propanediol), diethanolamine, lysine or ethylenediamine.

Salts containing an anion which is not pharmaceutically acceptable, such as, for example, trifluoroacetate, also belong within the scope of the invention as useful intermediates for preparing or purifying pharmaceutically acceptable salts and/or for use in nontherapeutic applications, for example in-vitro applications.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "physiologically functional derivative", denotes any physiologically acceptable derivative of a compound of the formula I according to the invention, e.g. an ester which is

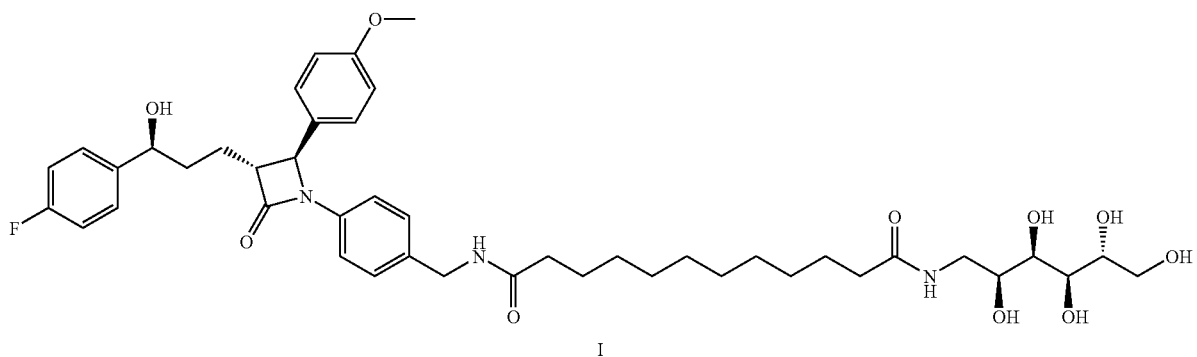

I and pharmaceutically acceptable salts thereof.

Because they are more soluble in water than the starting compounds or basis compounds, pharmaceutically acceptable salts are particularly suitable for medical applications. These salts must possess a pharmaceutically acceptable anion or cation. Suitable pharmaceutically acceptable acid addition salts of the compound according to the invention are salts of inorganic acids, such as hydrochloric acid, hydrobromic acid, phosphoric acid, metaphosphoric acid, nitric acid and sulfuric acid, and also of organic acids, such as acetic acid, benzenesulfonic acid, benzoic acid, citric acid, ethanesulfonic acid, able, on being administered to a mammal, such as a human, to form (directly or indirectly) a compound of the formula I or an active metabolite thereof.

The physiologically functional derivatives also include prodrugs of the compound according to the invention, as described, for example, in H. Okada et al., Chem. Pharm. Bull. 1994, 42, 57-61. Such prodrugs can be metabolized in vivo to give a compound according to the invention. These prodrugs may or may not themselves be active.

The compound according to the invention can also be present in different polymorphic forms, for example as amorphous and crystalline polymorphic forms. All the polymorphic forms of the compound according to the invention belong within the scope of the invention and are another aspect of the invention.

In that which follows, all references to "compound(s) according to formula I" relate to (a) compound(s) of the formula I as described above and to its (their) salts, solvates and physiologically functional derivatives as described herein.

An aryl radical is to be understood as meaning a phenyl, naphthyl, biphenyl, tetrahydronaphthyl, alpha- or beta-tetralone, indanyl or indan-1-onyl radical.

The compound(s) of the formula (I) can also be administered in combination with (an) other active compound(s).

The quantity of a compound according to formula I which is required in order to achieve the desired biological effect depends on a number of factors, e.g. the specific compound which is selected, the intended use, the type of administration and the clinical state of the patient. In general, the daily dose lies in a range from 0.01 mg to 100 mg (typically from 0.05 mg to 50 mg) per day per kilogram of body weight, e.g. 0.1-10 mg/kg/day.

Single dose formulations which can be administered orally, such as tablets or capsules, can, for example, contain from 1.0 to 1000 mg, typically from 10 to 600 mg. While the compounds according to formula I can themselves be used as the compound for treating the abovementioned conditions, they are preferably present, together with an acceptable carrier, in the form of a pharmaceutical composition. The carrier naturally has to be acceptable, in the sense that it is compatible with the other constituents of the composition and is not harmful to the health of the patient. The carrier can be a solid or a liquid or both and is preferably formulated with the compound as a single dose, for example as a tablet which can contain from 0.05% to 95% by weight of the active compound. Other pharmaceutically active substances can also be present, including other compounds according to formula I. The pharmaceutical compositions according to the invention can be prepared using one of the known pharmaceutical methods, which essentially consist in mixing the constituents with pharmacologically acceptable carrier substances and/or auxiliary substances.

Pharmaceutical compositions according to the invention are those which are suitable for oral and peroral (e.g. sublingual) administration even if the most suitable mode of administration depends, in each individual case, on the nature and severity of the condition to be treated and on the nature of the compound according to formula I which is in each case employed. Sugar-coated formulations and sugar-coated delayed-release formulations also belong within the scope of the invention. Formulations which are acid-resistant and gastric juice-resistant are preferred. Suitable gastric juice-resistant coatings include cellulose acetate phthalate, polyvinyl acetate phthalate, hydroxypropylmethyl cellulose phthalate and anionic polymers of methacrylic acid and methyl methacrylate.

Suitable pharmaceutical compounds for oral administration can be present in separate units, such as capsules, cachets, lozenges or tablets which in each case contain a specific quantity of the compound according to formula I; as powders or granulates; as a solution or suspension in an aqueous or non-aqueous liquid; or as an oil-in-water or a water-in-oil emulsion. As has already been mentioned, these compositions can be prepared using any suitable pharmaceutical method which includes a step in which the active compound and the carrier (which can consist of one or more additional constituents) are brought into contact. In general, the compositions are prepared by uniformly and homogeneously mixing the active compound with a liquid and/or finely divided solid carrier, after which the product is molded, if necessary. Thus, a tablet can be prepared, for example, by means of a powder or granulate of the compound being pressed or molded, where appropriate together with one or more additional constituents. Pressed tablets can be prepared by tableting the compound in freely flowing form, such as a powder or granulate, which is mixed, where appropriate, with a binder, lubricant, inert diluent and/or a (several) surface-active/dispersing agent(s) in a suitable machine. Molded tablets can be prepared by molding the pulverulent compound, which is moistened with an inert, liquid diluent, in a suitable machine.

Pharmaceutical compositions which are suitable for peroral (sublingual) administration include lozenges which contain a compound according to formula I together with a flavoring agent, usually sucrose and gum arabic or tragacanth, and pastils, which include the compound in an inert base such as gelatin and glycerol or sucrose and gum arabic.

The following are suitable to use as additional active compounds for the combination preparations:

all the antidiabetics which are named in chapter 12 in the Roten Liste [Red List] 2003. They can be combined with compounds of the formula I according to the invention, particularly for the purpose of synergistically improving the effect. The active compound combination can be administered either by separately administering the active compounds to the patient or administering them in the form of combination preparations in which several active compounds are present in one pharmaceutical preparation. Most of the active compounds which are cited below are disclosed in USP Dictionary of USAN and International Drug Names, US Pharmacopeia, Rockville 2001.

Antidiabetics include insulin and insulin derivatives, such as Lantus® (see www.lantus.com) or HMR 1964, rapidly acting insulins (see U.S. Pat. No. 6,221,633), GLP-1 derivatives, such as those which Novo Nordisk A/S has disclosed in WO 98/08871, Zealand has disclosed in WO/04156 and Beaufour-Ipsen has disclosed in WO 00/34331 and also orally active hypoglycaemic active compounds.

The orally active hypoglycaemic active compounds preferably include sulfonylureas, biguanidines, meglitinides, oxadiazolidinediones, thiazolidinediones, glucosidase and glycogen phosphorylase inhibitors, glucagon antagonists, GLP-1-agonists, potassium channel openers, such as those which Novo Nordisk A/S has disclosed in WO 97/26265 and WO 99/03861, insulin sensitizers, inhibitors of liver enzymes which are involved in stimulating gluconeogenesis and/or glycogenolysis, modulators of glucose uptake, glucose transport and glucose reabsorption, compounds which alter fat metabolism, such as antihyperlipidaemic active compounds and antilipidaemic active compounds, compounds which decrease food intake, PPAR agonists and PXR agonists, and active compounds which act on the ATP-dependent potassium channel in the beta cells.

In one embodiment of the invention, the compounds of the formula I are administered in combination with an HMGCoA reductase inhibitor, such as simvastatin, fluvastatin, pravastatin, lovastatin, atorvastatin, cerivastatin or rosuvastatin.

In one embodiment of the invention, the compounds of the formula I are administered in combination with a cholesterol absorption inhibitor, such as ezetimibe, tiqueside or pamaqueside.

In one embodiment of the invention, the compounds of the formula I are administered in combination with a PPAR gamma agonist, such as rosiglitazone, pioglitazone, JTT-501 or GI 262570.

In one embodiment of the invention, the compounds of the formula I are administered in combination with a PPAR alpha agonist, such as GW 9578 or GW 7647.

In one embodiment of the invention, the compounds of the formula I are administered in combination with a mixed PPAR alpha/gamma agonist, such as GW 1536, AVE 8042, AVE 8134 or AVE 0847, or as described in PCT/US/11833, PCT/US/11490 or DE10142734.4.

In one embodiment of the invention, the compounds of the formula I are administered in combination with a fibrate, such as fenofibrate, clofibrate or bezafibrate.

In one embodiment of the invention, the compounds of the formula I are administered in combination with an MTP inhibitor, such as implitapide, BMS-201038 or R-103757.

In one embodiment of the invention, the compounds of the formula I are administered in combination with a bile acid absorption inhibitor (see, e.g., U.S. Pat. No. 6,245,744 or U.S. Pat. No. 6,221,897), such as HMR 1741.

In one embodiment of the invention, the compounds of the formula I are administered in combination with a CETP inhibitor, such as JTT-705.

In one embodiment of the invention, the compounds of the formula I are administered in combination with a polymeric bile acid adsorber, such as cholestyramine or colesevelam.

In one embodiment of the invention, the compounds of the formula I are administered in combination with an LDL receptor inducer (see U.S. Pat. No. 6,342,512), such as HMR1171 or HMR 1586.

In one embodiment of the invention, the compounds of the formula I are administered in combination with an ACAT inhibitor, such as avasimibe.

In one embodiment of the invention, the compounds of the formula I are administered in combination with an antioxidant, such as OPC-14117.

In one embodiment of the invention, the compounds of the formula I are administered in combination with a lipoprotein lipase inhibitor, such as NO-1886

In one embodiment of the invention, the compounds of the formula I are administered in combination with an ATP citrate lyase inhibitor, such as SB-204990.

In one embodiment of the invention, the compounds of the formula I are administered in combination with a squalene synthetase inhibitor, such as BMS-188494.

In one embodiment of the invention, the compounds of the formula I are administered in combination with a lipoprotein (a) antagonist, such as CI-1027 or nicotinic acid.

In one embodiment of the invention, the compounds of the formula I are administered in combination with a lipase inhibitor, such as orlistat.

In one embodiment of the invention, the compounds of the formula I are administered in combination with insulin.

In one embodiment, the compounds of the formula I are administered in combination with a sulfonylurea, such as tolbutamide, glibenclamide, glipizide or glimepiride.

In one embodiment, the compounds of the formula I are administered in combination with a biguanide, such as metformin.

In yet another embodiment, the compounds of the formula I are administered in combination with a meglitinide, such as repaglinide.

In one embodiment, the compounds of the formula I are administered in combination with a thiazolidinedione, such as troglitazone, ciglitazone, pioglitazone, rosiglitazone or the compounds disclosed by Dr. Reddy's Research Foundation in WO 97/41097, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with an α-glucosidase inhibitor, such as miglitol or acarbose.

In one embodiment, the compounds of the formula I are administered in combination with an active compound which acts on the ATP-dependent potassium channel of beta cells, such as tolbutamide, glibenclamide, glipizide, glimepiride or repaglinide.

In one embodiment, the compounds of the formula I are administered in combination with more than one of the abovementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In another embodiment, the compounds of the formula I are administered in combination with CART modulators (see "cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid-{4-[(4-aminoquinazolin-2-ylamino)methyl] cyclohexylmethyl}amide hydrochloride (CGP 71683A)), cannabinoid receptor 1 antagonists (see, e.g., EP 0656354, WO 00/15609 or WO 02/076949) MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl] amide; (WO 01/91752)), orexin antagonists (e.g. 1-(2-methylbenzoxazol-6-yl)-3-[1,5]naphthyridin-4-yl urea hydrochloride (SB-334867-A)), H3 agonists (3-cyclohexyl-1-(4,4-dimethyl-1,4,6,7-tetrahydroimidazo[4,5-c]pyridin-5-yl)-propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, β3-agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), MSH (melanocyte-stimulating hormone) agonists, MCH (melanin-concentrating hormone) receptor antagonists (see, e.g., WO 03/15769), CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), or SR-146131 (WO 0244150) or SSR-125180), serotonin reuptake inhibitors (e.g. dexfenfluramine), mixed serotoninergic and noradrenergic compounds (e.g. WO 00/71549), 5HT agonists, e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (tert-butyl 6-benzyloxy-1-(2-diisopropylaminoethylcarbamoyl)-3,4-dihydro-1H-isoquinoline-2-carboxylate (WO 01/85695)), TRH agonists (see, e.g. EP 0 462 884) uncoupling protein 2 or protein 3 modulators, leptin agonists (see, e.g. Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, doprexin), lipase/amylase inhibitors (erg. WO 00/40569), PPAR modulators (e.g. WO 00/78312), 11β-HSD1 (11-beta-hydroxysteroiddehydrogenase type 1) inhibitors (see e.g. WO 01/90094 or T. Barf et al., J. Med.

Chem. (2002), 45, 3813-3815), acetyl-CoA carboxylase (ACC; see e.g. WO 99/46262) inhibitors, dipeptidylpeptidase IV (DPP-IV; see e.g. EP 1259246) inhibitors, RXR modulators or TR-β-agonists.

In one embodiment of the invention, the other active compound is leptin; see, e.g., "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active compound is dexamphetamine or amphetamine.

In one embodiment, the other active compound is fenfluramine or dexfenfluramine.

In yet another embodiment, the other active compound is sibutramine.

In one embodiment, the other active compound is orlistat.

In one embodiment, the other active compound is mazindol or phentermine.

In one embodiment, the compounds of the formula I are administered in combination with ballast substances, preferably insoluble ballast substances (see, e.g., carob/Caromax®) (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Hoechst, 65926 Frankfurt/Main)). The combination with Caromax® can be effected in one preparation or by means of separating administering compounds of the formula I and Caromax®. In this connection, Caromax® can also be administered in the form of foodstuffs, for example in bread, cakes and pastries or muesli bars.

It will be understood that each suitable combination of the compounds according to the invention with one or more of the abovementioned compounds and, if desired, one or more additional pharmacologically active substances, is regarded as coming within the protected scope of the present invention.

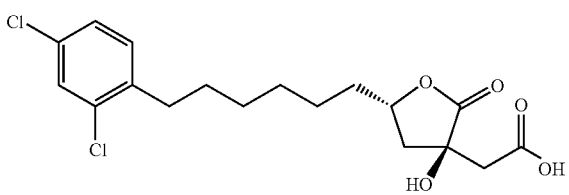

SB-204990

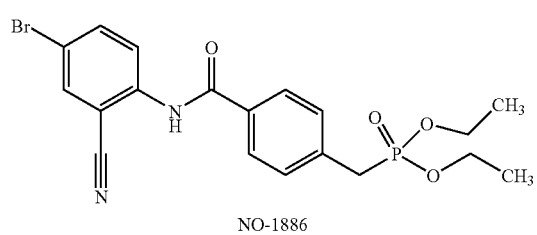

NO-1886

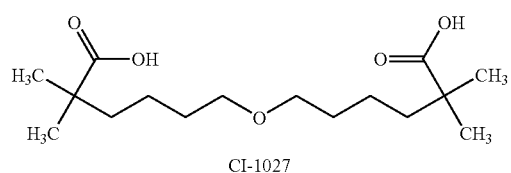

CI-1027

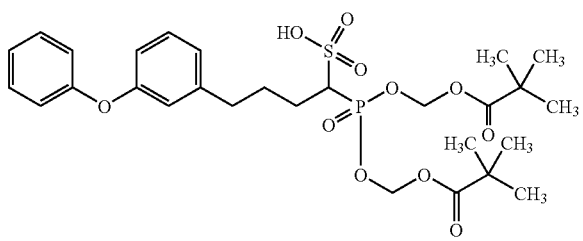

BMS-188494

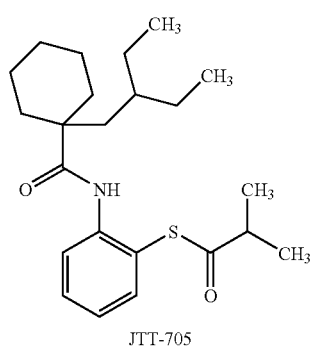

JTT-705

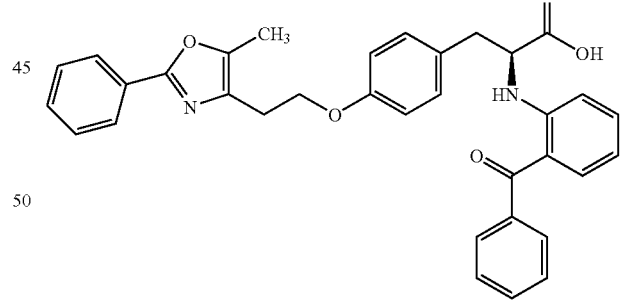

GI 262570

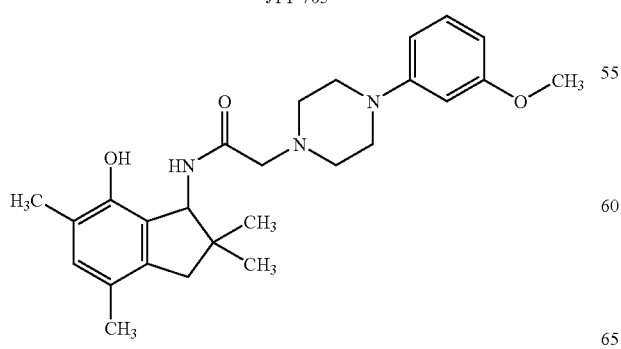

OPC-14117

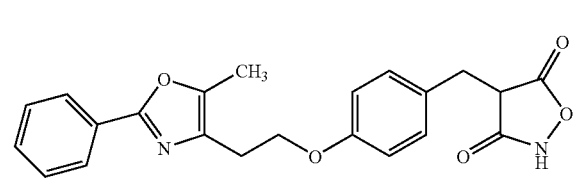

JTT-501

The invention also relates to processes for preparing the compound of the formula I.

Process A:

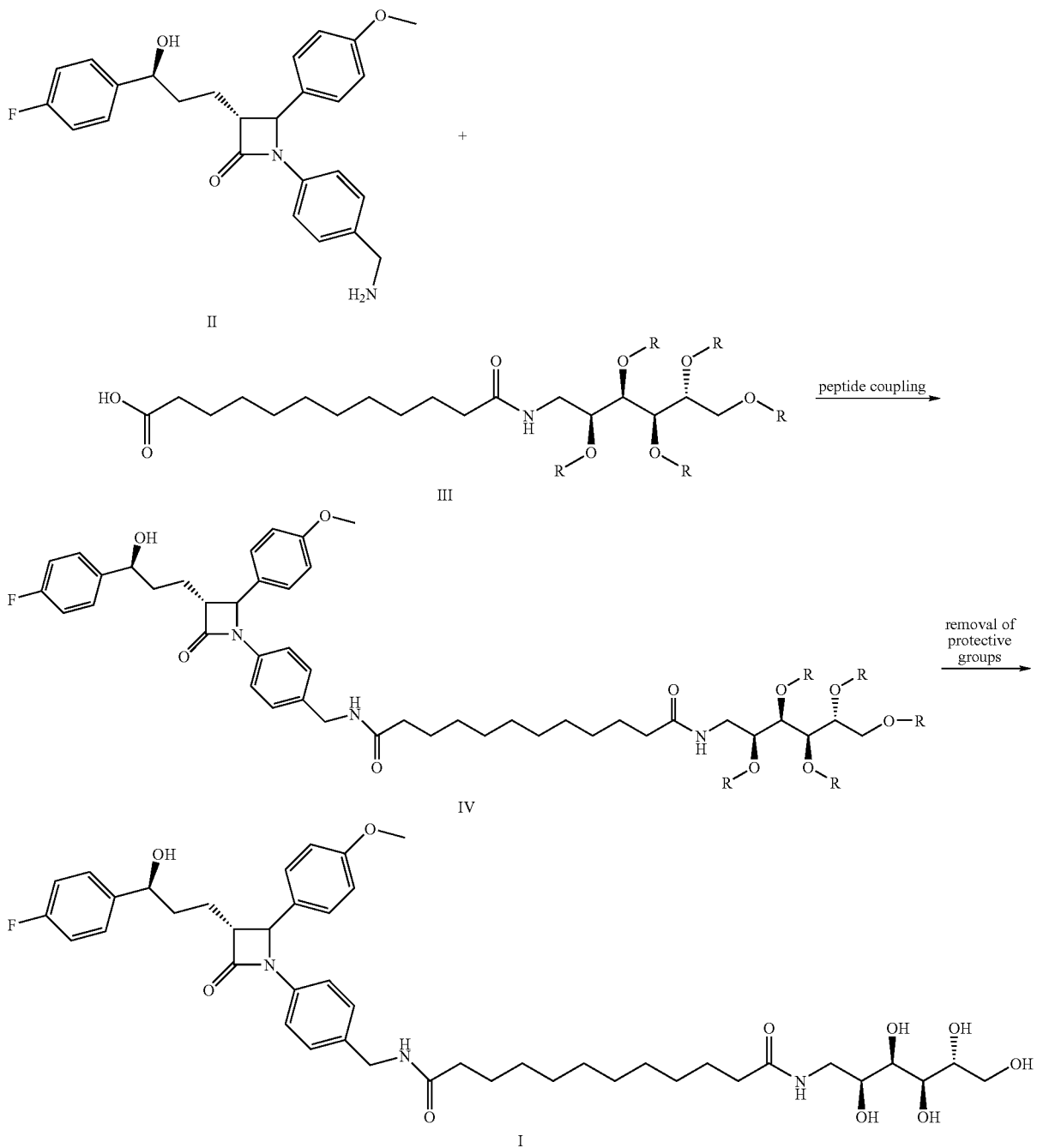

Process A for preparing the compound of the formula I is characterized in that the amine of the formula II (see WO 02/50027) is, in a peptide coupling reaction, reacted with the monoglucamide of 1,12-dodecanedicarboxylic acid (formula III where the hydroxyl functions of the glucamine moiety may be protected, for example by acyl groups such as acetyl groups or by ether groups such as benzyl ether groups, to give a compound of the formula IV. This reaction can be carried out using, for example, N-hydroxy-benzotriazole (HOBt) and N-ethyl-N'-(3-dimethylaminopropyl)carbodiimide (EDC) at room temperature, using, for example, as solvent dimethylformamide (DMF). It is also possible to use other peptide coupling reagents and solvents or solvent mixtures (seer for example, A. Speicher et al. in Journal für Praktische Chemie/Chemiker-Zeitung (1998), 340, 581-583; Y. S. Klausner and M. Bodansky, Synthesis, (1972), 453 ff; K. Ishihara et al., J. Org. Chem., 61, 4196 (1996); M. Kunishima et al., Tetrahedron 55, 13159-13170 (1999) or else R. C. Larock: Comprehensive Organic Transformations; VCH, New York, 1989, page 981 ff).

Process B:
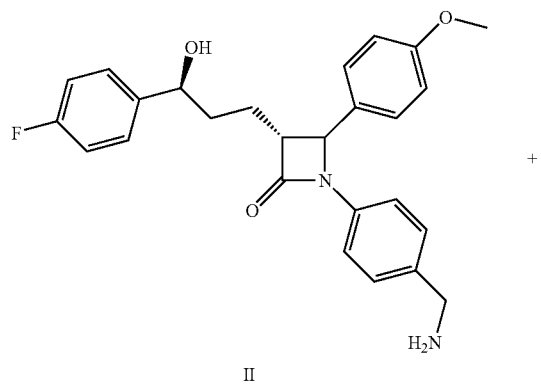
II
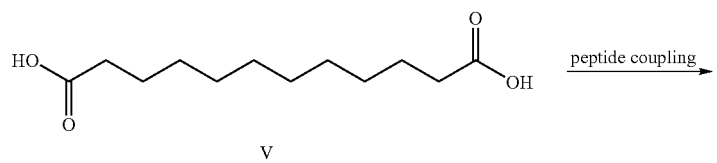
V
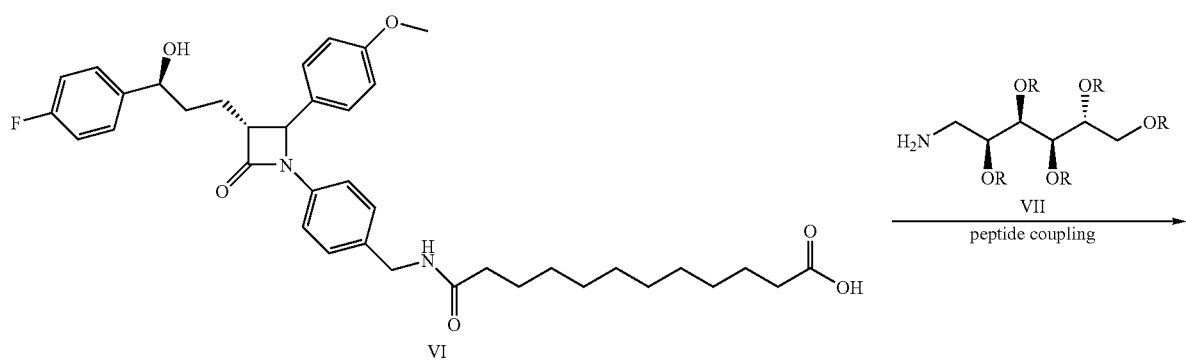
VI
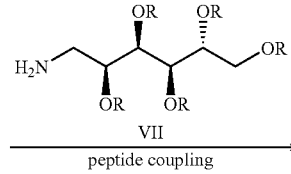
VII
peptide coupling
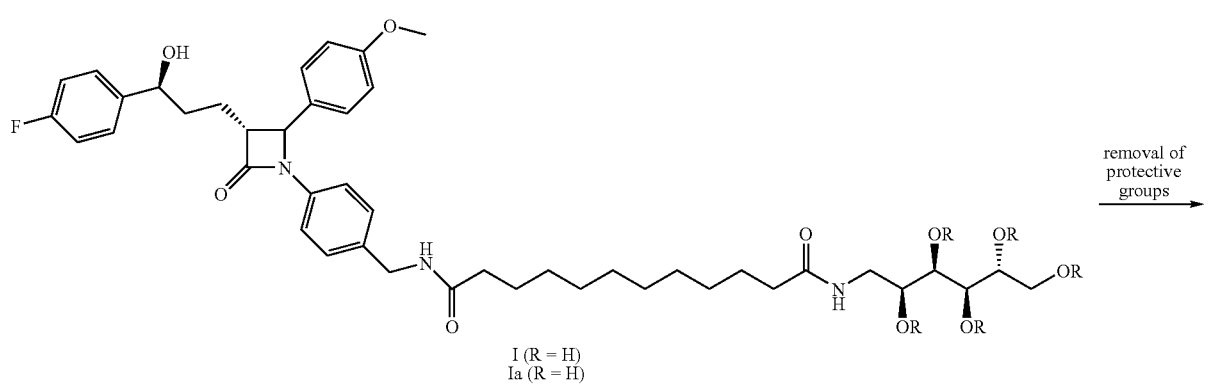
I (R = H)
Ia (R = H)
removal of protective groups -continued

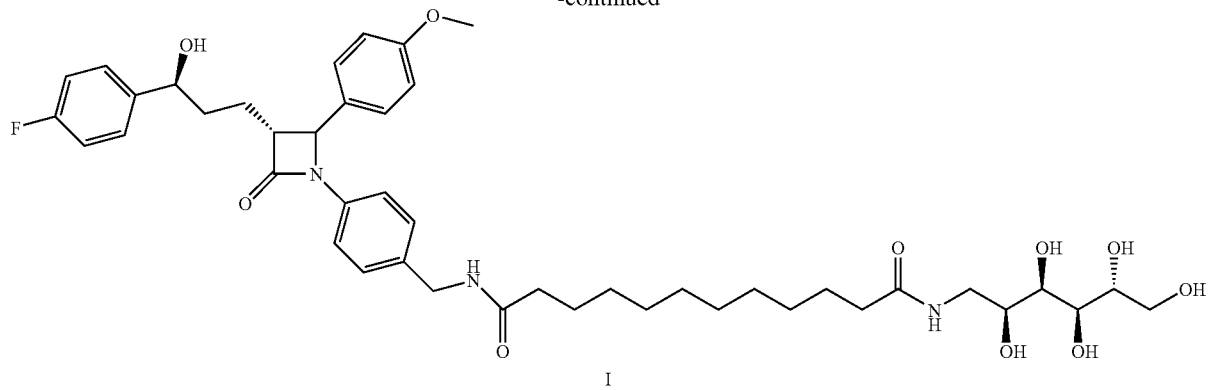

I

A further process (B) according to the invention comprises reacting the amine of the formula II with 1,12-dodecanedicarboxylic acid V under peptide coupling conditions and further reacting the product of the formula VI with glucamine VII, whose hydroxyl functions may carry protective groups (for example acetyl protective groups or benzyl protective groups), again under peptide coupling conditions, to give the compound of the formula I or the corresponding compound Ia which carries protective groups. In a further step, the protective groups may be removed either under weakly alkaline conditions, for example dilute aqueous ammonia, or hydrogenolytically (in the case of benzyl ether protective groups being used) to give the compound of the formula I.

Process C:

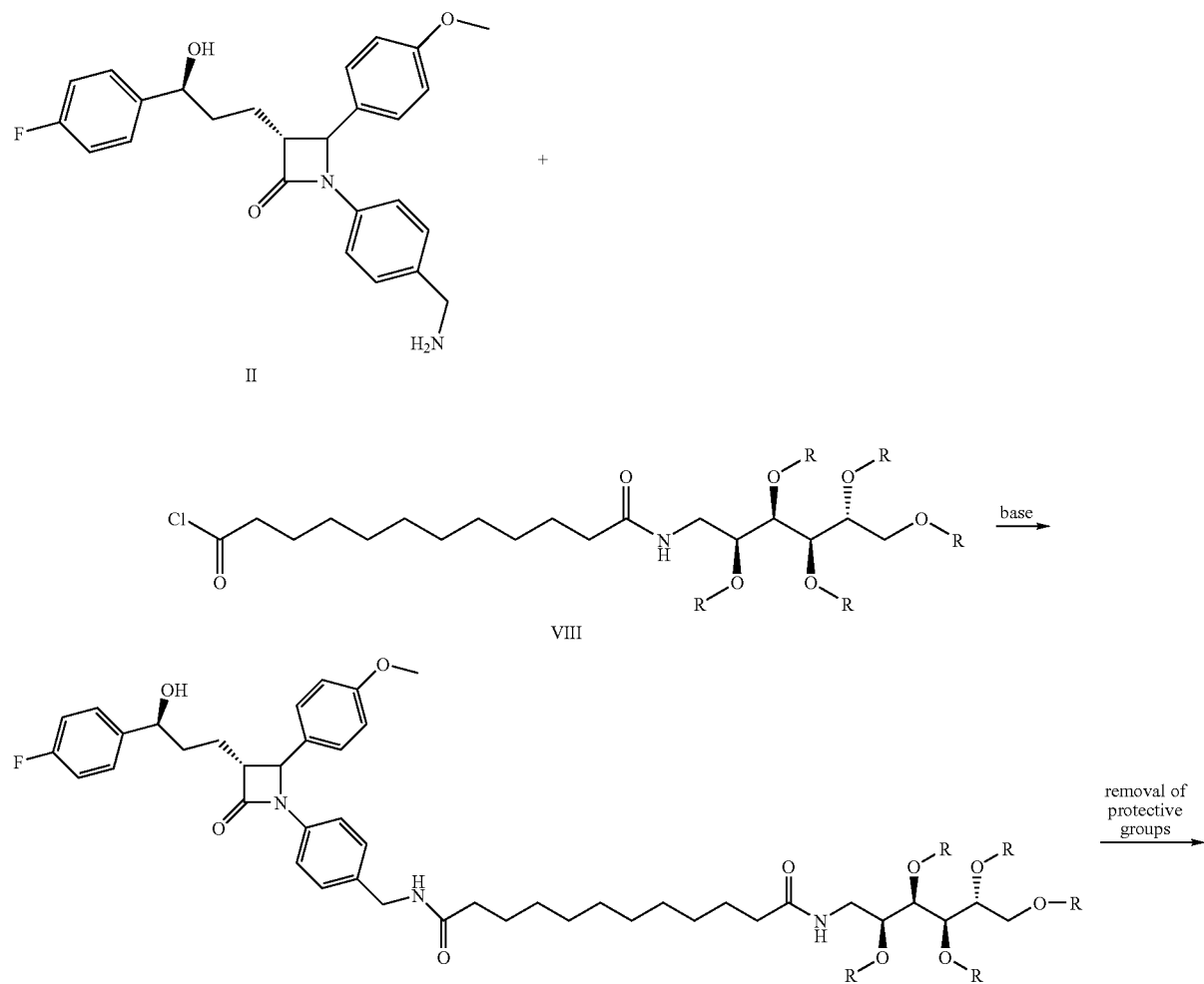

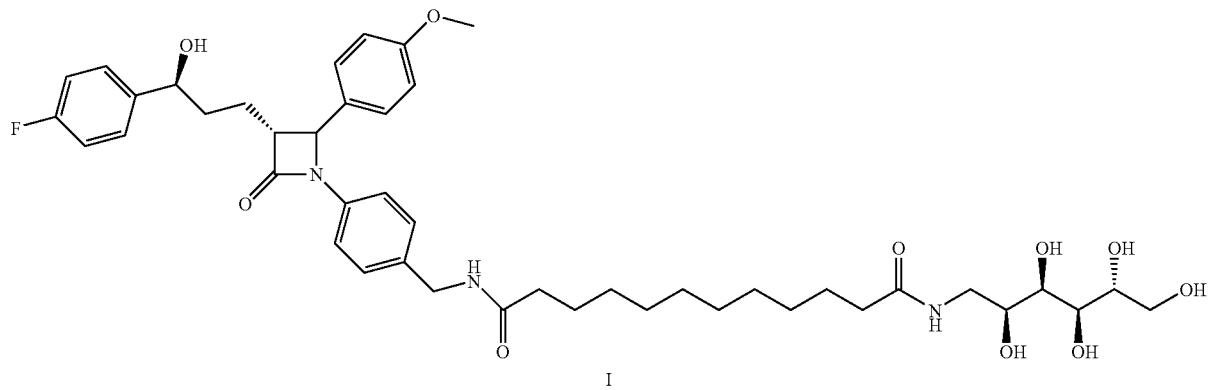

In a further process C according to the invention, the amine of the formula II is reacted with an acid halide, for example the chloride of 11-((4R,6R)-4,5,6-trihydroxy-3-(R)-hydroxy-2-(S)-hydroxyhexylcarbamoyl)-undecanoic acid VIII, for example in pyridine or in dichloromethane, with or without addition of amine base, at room temperature. Here, the hydroxyl functions of the glucamine moiety advantageously carry the abovementioned protective groups which may, after coupling to give the amide of the formula Ia, be removed.

The invention furthermore relates to the intermediates of formulae III, IV and VIII wherein R is acyl, for example acetyl or benzoyl, or in which R is aralkyl, alkyl or aryl, for example benzyl.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

EXAMPLE I

Process A1

1.) Monomethyl Dodecanedioate

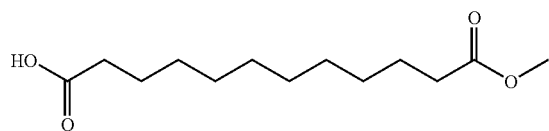

With heating, 4.6 g (20 mmol) of dodecanoic acid are dissolved in 40 ml of dry THF, 0.73 ml (10 mmol) of thionyl chloride is added slowly and the mixture is stirred at RT for 30 min. 0.8 ml (20 mmol) of dry methanol is then added slowly and the mixture is stirred at RT for 4 h; the mixture is then allowed to stand at RT for 4 days. After this period of time, TLC shows no further conversion; the reaction mixture is concentrated under reduced pressure and the residue is triturated with water (ultrasonic bath). The precipitate is filtered off with suction, washed with water and again filtered off with suction. The moist residue is triturated with dichloromethane (ultrasonic bath), filtered through a pleated filter and washed with dichloromethane, and the filtrate is concentrated under reduced pressure. This gives monomethyl dodecanedioate (3.09 g) in a yield of 63%. MW: 244.34; MS: 245.4 (M+H$^+$).

2.) Synthesis of methyl 11-((4R,6R)-4,5,6-trihydroxy-3-(R)-hydroxy-2-(S)-hydroxyhexylcarbamoyl)undecanoate At room temperature, 3.07 g (12.6 mmol) of monomethyl dodecane-dioate are dissolved in 30 ml of dry DMF, 2.2 g (12.1 mmol) of glucamine, 1.9 g (12.4 mmol) of HOBt and 2.4 g (12.5 mmol) of EDC are added and the mixture is stirred at RT for 6 h. The mixture is allowed to stand at RT overnight. The next day, TLC shows complete conversion. The reaction mixture is concentrated under reduced pressure and dried under high vacuum. The residue is triturated with water (ultrasonic bath), filtered off with suction, washed with water and filtered off with suction. The moist crude product is triturated with dichloromethane, filtered off with suction, washed with dichloromethane and dried. This gives methyl 11-((4R,6R)-4,5,6-trihydroxy-3-(R)-hydroxy-2-(S)-hydroxyhexyl-carbamoyl)undecanoate. 4.45 g (90% yield). MW: 407.51; MS: 408.20 (M+H$^+$).

3.) Synthesis of 11-((4R,6R)-4,5,6-trihydroxy-3-(R)-hydroxy-2-(S)-hydroxyhexylcarbamoyl)undecanoic acid (III; R=H)

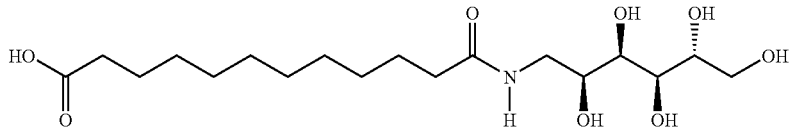

At room temperature, 4.45 g (10.9 mmol) of methyl 11-((4R,6R)-4,5,6-trihydroxy-3-(R)-hydroxy-2-(S)-hydroxyhexyl-carbamoyl)undecanoate are suspended in 75 ml of dry ethanol, and 25 ml of water and 2.2 g of KOH (85% strength) (33 mmol) are added. After 2 h of stirring at 80° C., TLC shows complete conversion. The reaction mixture is concentrated under reduced pressure; the residue is dissolved in water and acidified with conc. hydrochloric acid. The precipitated crude product is filtered off with suction, washed with water and filtered off with suction. The moist crude product is recrystallized from about 100 ml of ethanol, filtered while hot and precipitated in an ice bath. The precipitate is filtered off with suction, washed with ethanol and dried. This gives 2.2 g (51%) of 11-((4R,6R)-4,5,6-trihydroxy-3-(R)-hydroxy-2-(S)-hydroxyhexyl-carbamoyl)undecanoic acid. MW: 393.48; MS: 394.28 (M+H$^+$).

4.) Synthesis of dodecanedioic acid 4-[(2S,3R)-3-[(S)-3-(4-fluorophenyl)-3-hydroxypropyl]-2-(4-methoxyphenyl)-4-oxoazetidin-1-yl]benzylamide ((2S,3R,4R,5R)-2,3,4,5,6-pentahydroxyhexyl)amide (I)

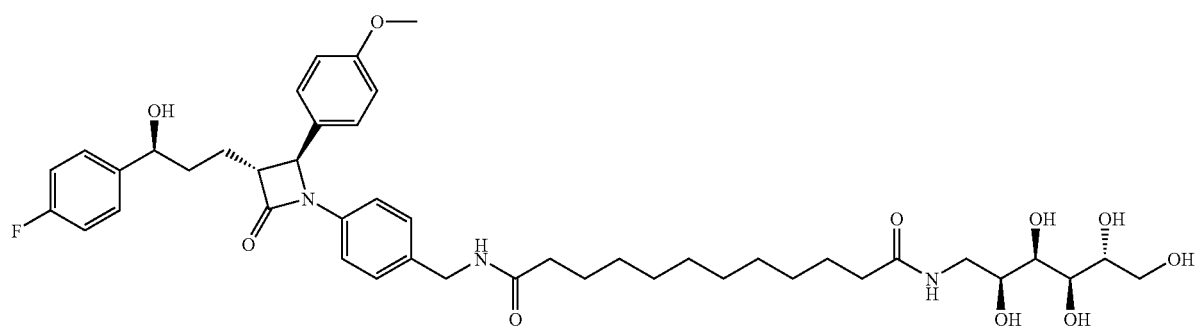

With gentle heating, 0.63 g (1.45 mmol) of benzylamine II (preparation see DE 10064398) and 0.65 g (1.65 mmol) of the diacid monoamide (see above) are dissolved in 15 ml of dry DMF, 0.25 g (1.63 mmol) of HOBt and 0.31 g (1.67 mmol) of EDC are added and the mixture is stirred at RT for 4 h. The reaction mixture is allowed to stand at RT overnight. The next morning, TLC shows complete conversion. The reaction mixture is concentrated under reduced pressure and the residue is dried under high vacuum. The residue is triturated with water (ultrasonic bath), filtered off with suction, washed with water and filtered off with suction. The crude product is recrystallized from isopropanol. The crystals are finally triturated with water, filtered off with suction and dried. This gives 0.38 g (32%) of dodecanedioic acid 4-[(2S,3R)-3-[(S)-3-(4-fluorophenyl)-3-hydroxy-propyl]-2-(4-methoxyphenyl)-4-oxoazetidin-1-yl]benzylamide ((2S,3R,4R,5R)-2,3,4,5,6-pentahydroxyhexyl)amide (I). MW: 809.97; MS: 810.49 (M+H$^+$).

Process A2

1.) 11-((2S,3R,4R,5R)-2,3,4,5,6-pentaacetoxyhexylcarbamoyl)-undecanoic acid (III; R=acetyl)

At room temperature, 87 mg of amine II are dissolved in 3 ml of dried dimethylformamide, and 120 mg of the carboxylic acid described above, 31 mg of N-hydroxybenzotriazole and 39 mg of N-ethyl-N'-(3-dimethylaminopropyl)carbodiimide are added. The reaction mixture is stirred at room temperature overnight and then concentrated under reduced pressure The residue is taken up in ethyl acetate and the organic phase is washed with water and dried over magnesium sulfate. The mixture is then filtered and the filtrate is concentrated under reduced pressure. This gives 90 mg of (2R,3R,4R,5S)-2,3,4,5-tetraacetoxy-6-(11-{4-[(2S,3R)-3-[(S)-3-(4-fluorophenyl)-3-hydroxypropyl]-2-(4-methoxyphenyl)-4-oxoazetidin-1-yl]benzylcarbamoyl}undecanoylamino)hexyl acetate. MW: 1020.16.

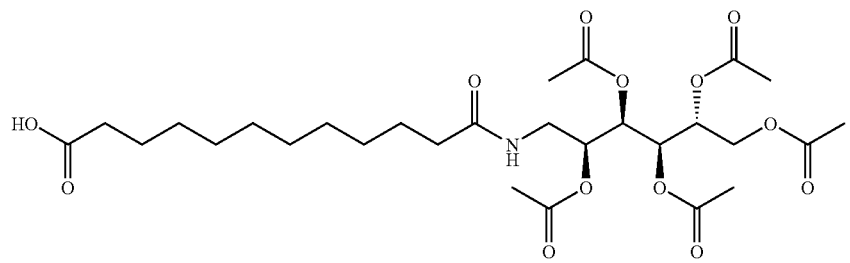

At room temperature, 3 ml of dry pyridine and 3 ml of acetic anhydride are added to 0.4 g of 11-((4R,6R)-4,5,6-trihydroxy-3-(R)-hydroxy-2-(S)-hydroxyhexylcarbamoyl) undecanoic acid (III; R=H), and the mixture is stirred at room temperature for 4 h. After the reaction has ended, water is added to the reaction mixture and the mixture is concentrated under reduced pressure. The residue is triturated with a little water and filtered. The filter residue is washed with water and then dried under reduced pressure. This gives 0.56 g of 11-((2S,3R,4R,5R)-2,3,4,5,6-pentaacetoxyhexylcarbamoyl)-undecanoic acid. MW: 603.66; MS: 604.22 (M+H$^+$).

2.) (2R,3R,4R,5S)-2,3,4,5-tetraacetoxy-6-(11-{4-[(2S,3R)-3-[(S)-3-(4-fluorophenyl)-3-hydroxypropyl]-2-(4-methoxyphenyl)-4-oxoazetidin-1-yl] benzylcarbamoyl}undecanoylamino)hexyl acetate (IV; R=acetyl)

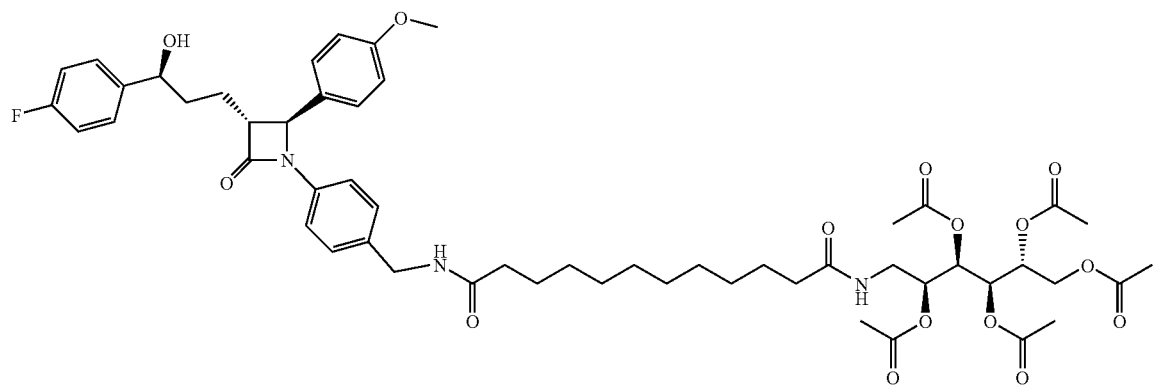

3.) Dodecanedioic acid 4-[(2S,3R)-3-[(S)-3-(4-fluorophenyl)-3-hydroxy-propyl]-2-(4-methoxyphenyl)-4-oxoazetidin-1-yl]benzylamide ((2S,3R,4R,5R)-2,3,4,5,6-pentahydroxyhexyl)amide (I)

h. The reaction solution is concentrated and separated by HPLC (Knauer Eurospher-100-10-C18, water (0.1% trifluoroacetic acid)/acetonitrile (0.1% trifluoroacetic acid)=80/20→10/90). This gives the product of molecular weight 646.81 ($C_{38}H_{47}F_1N_2O_6$); MS (ESI) 647.35 (M+H$^+$)

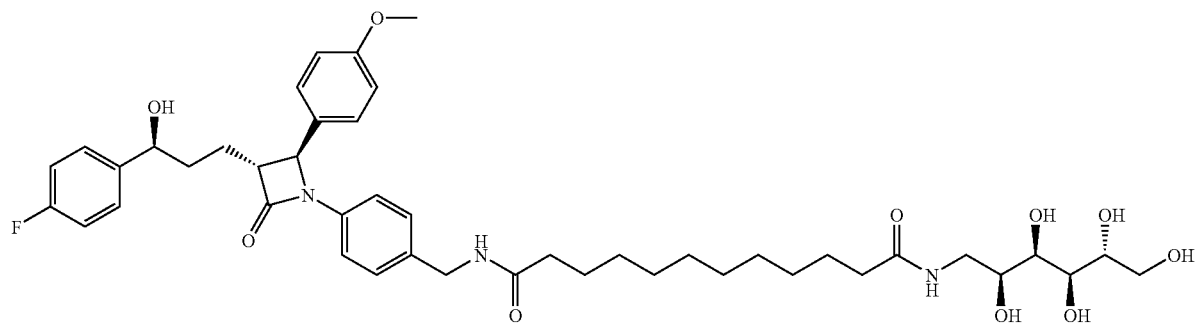

90 mg of the compound described above are treated with guanidine in a mixture of ethanol and dichloromethane. This gives the glucamine derivative I of MW 809.97.

Process B

1.) 11-{4-[(2S,3R)-3-[(S)-3-(4-fluorophenyl)-3-hydroxypropyl]-2-(4-methoxyphenyl)-4-oxoazetidin-1-yl]benzylcarbamoyl}undecanoic acid (VI)

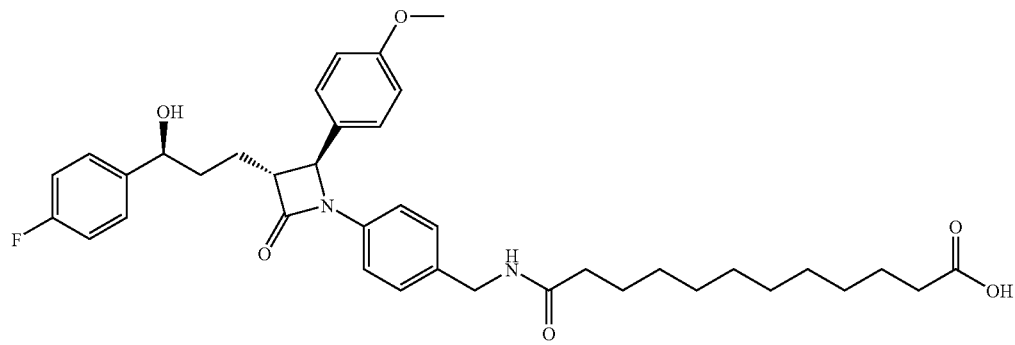

A solution of 70 mg of amine I and 23 µl of triethylamine in 1 ml of dimethylformamide is added to a solution of 371 mg of dodecanedioic acid, 63 µl of diisopropylcarbodiimide and 55 mg of hydroxybenzotriazole in 2 ml of dimethylformamide, and the mixture is stirred at room temperature for 12

2.) Dodecanedioic acid 4-[(2S,3R)-3-[(S)-3-(4-fluorophenyl)-3-hydroxypropyl]-2-(4-methoxyphenyl)-4-oxoazetidin-1-yl]benzyl-amide ((2S,3R,4R,5R)-2,3,4,5,6-pentahydroxyhexyl)amide (I)

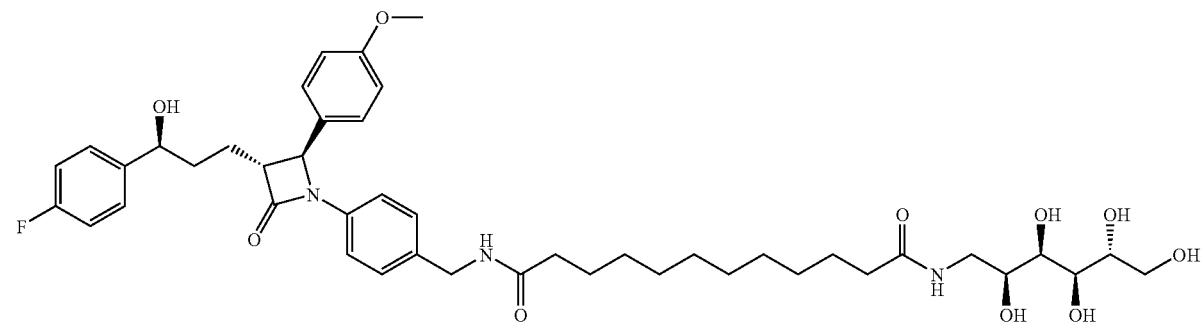

I

As described above for other coupling reactions, reaction of acid VI with glucamine (VII; R=H) and HOBt/EDC in DMF gives the compound I (R=H).

If, instead of glucamine, a protected glucamine derivative, for example VII (R=acetyl) is used, the compound Ia where R=acetyl is obtained.

Process C

1.) (2R,3R,4R,5R)-2,3,4,5-tetraacetoxy-6-(11-chlorocarbonyl-undecanoylamino)hexyl acetate (VIII; R=acetyl)

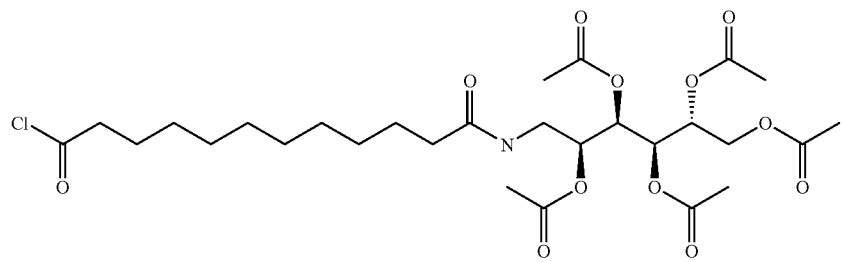

The compound of the formula III (R=acetyl) is dissolved in tetrahydrofuran and thionyl chloride is added slowly; the mixture is stirred at room temperature for 1 h. The reaction solution is then concentrated under reduced pressure and the crude product is used for the next step.

2.) (2R,3R,4R,5S)-2,3,4,5-tetraacetoxy-6-(11-{4-[(2S,3R)-3-[(S)-3-(4-flurophenyl)-3-hydroxypropyl]-2-(4-methoxyphenyl)-4-oxoazetidin-1-yl] benzylcarbamoyl}undecanoylamino)hexyl acetate (IV; R=acetyl)

fed with a standard diet (Altromin, Lage (Lippe)). The afternoon prior to the administration of the radioactive tracers ($^{14}$C-cholesterol), the feed is removed and the animals are adapted to grates.

Additionally, the animals are labeled s.c with $^{3}$H-TCA (taurocholic acid) (for example 1 µCi/mouse up to 5 µCi/rat) 24 hours prior to the peroral administration of the test meal ($^{14}$C-cholesterol in Intralipid® 20, Pharmacia-Upjohn).

Cholesterol absorption test: 0.25 ml/mouse Intralipid® 20 (Pharmacia-Upjohn) ((spiked with 0.25 µCi of $^{14}$C-cholesterol in 0.1 mg of cholesterol) is administered perorally by gavage.

Test substances are prepared separately in 0.5%/(methylcellulose (Sigma)/5% Solutol (BASF, Ludwigshafen) or a suitable vehicle.

The administration volume of the test substance is 0.5 ml/mouse. The test substance is administered immediately prior to the test meal (Intralipid labeled with $^{14}$C-cholesterol) (cholesterol absorption test).

The feces are collected over a period of 24 h: fecal elimination of $^{14}$C-cholesterol and $^{3}$H-taurocholic acid (TCA) is determined after 24 hours.

IV

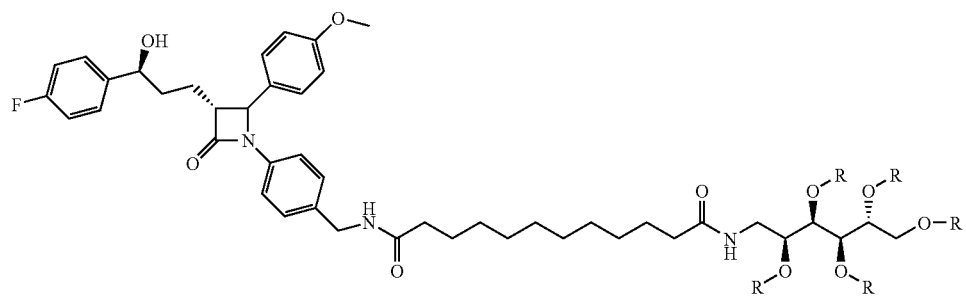

At room temperature, amine I is added to the acid chloride shown above in a mixture of pyridine and dichloromethane, and the mixture is stirred at room temperature overnight. Work-up gives amide IV where R=acetyl.

Using the method described below, the activity of the compound of the formula I according to the invention was examined:

Effect on Cholesterol Absorption+$^{3}$H-Taurocholic Acid Excretion Using Fecal Excrement of Mice, Rats or Hamsters NMRI mice, Wistar rats, or Golden Syrian hamsters (in groups of n=4-6) are kept in metabolic cages, where they are The livers are removed and homogenized, and aliquots are incinerated in an oximate (Model 307, Packard) to determine the amount of $^{14}$C-cholesterol which had been taken up/absorbed.

Evaluation:

Feces Samples:

The total weight is determined, the sample is made up with water to a defined volume and then homogenized, and an aliquot is evaporated to dryness and incinerated in an oximate (Model 307 from Packard for the incineration of radioactively labeled samples): the amount of radioactive $^3H$—H2O and $^{14}C$—CO2 is extrapolated to the amount of $^3H$-taurocholic acid and $^{14}C$-cholesterol, respectively, that is excreted (dual isotope technique). The $ED_{200}$ values as dose from a dose-effect curve are interpolated as those doses at which the excretion of TCA or cholesterol is doubled, based on a control group treated at the same time.

Liver Samples:

The amount of $^{14}C$-cholesterol taken up by the liver is based on the administered dose. The $ED_{50}$ values are interpolated from a dose-effect curve as the dose at which the uptake of $^{14}C$-cholesterol by the liver is halved (50%), based on a control group.

The $ED_{50}$ value below demonstrates the activity of the compound of the formula I according to the invention

| Example No. | $ED_{50}$ (liver) [mg/mouse] |
|---|---|
| I | 0.005 |

As can be seen from the table, the compound of the formula I has very good cholesterol-lowering action.

The solubility of compound I and of the comparative compound C1 was tested as follows:

The comparative compound selected was the compound from WO 02/50027 with the most similar structure:

0.5 mg of the compound to be tested was weighed exactly into an Eppendorf cap, and 0.5 ml of the solvent in question (aqueous buffer) was added. The Eppendorf cap was then introduced into a thermomixer and, at 25° C., shaken at 1 400 rpm for 4 hours.

The Eppendorf cap was then introduced into a centrifuge. Following centrifugation, an aliquot of the supernatant was used to determine the amount dissolved, using HPLC/UV analysis. The table below shows the results obtained:

| pH conditions | Example 1 Solubility in µg/ml | C1 Solubility in µg/ml |
|---|---|---|
| Water (pH) | 3 (6.8) | <1 |
| pH 1.2 | 3 | <1 |
| pH 4.5 | 4 | <1 |
| pH 6.8 | 2 | <1 |
| pH 8.0 | 2 | <1 |

-continued

| pH conditions | Example 1 Solubility in µg/ml | C1 Solubility in µg/ml |
|---|---|---|
| FaSSIF | 28 | 5 |
| FeSSIF | 454 | 18 |

In the physiological solvents FaSSIF and FeSSIF (composition and preparations see Physiologically based dissolution tests—Experiences with poorly soluble drugs, January 2000, Shaker, ISBN: 3-8265-6962-8) the solubility of example 1 was determined as being 28 and 454 µg/ml, respectively, whereas the corresponding values for C1 were 5 and 18 µg/mi, respectively. This significantly different solubility could also be confirmed during a repetition of the tests (43/290 µg/ml compared to 6/20 µg/ml).

Accordingly, the compound of the formula I according to the invention has a 6-fold to 16-fold better solubility than the comparative compound of the formula C1. Accordingly, the compound of the formula I according to the invention has better availability in dissolved form at the site of action. In contrast to the more poorly soluble substances, even any higher doses can be provided completely for interaction with

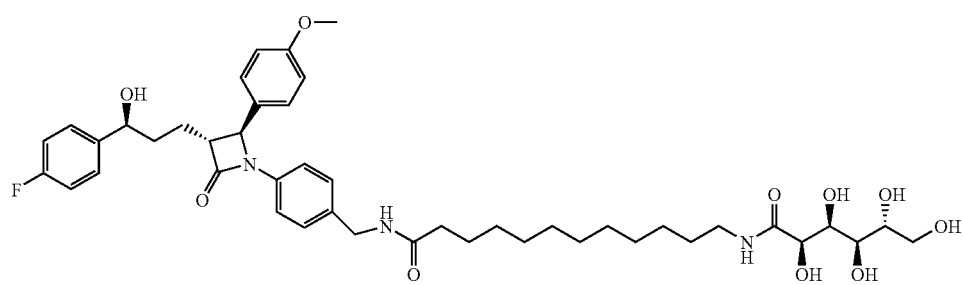

C1 the transport system in question. Based on an available volume of 250 ml (Biopharmaceutical Classification System), doses of up to ~100 mg are soluble, whereas in the case of C1 in the best case only doses in the range of 5 mg would be soluble (in the worst case even only: 1.25 mg).

The stability of compound 1 and that of the comparative compound C1 in solution was tested as follows:

The stability of dissolved compound I and of dissolved C1 was determined in aqueous buffers in the pH range 1.2-8.0. 1 mg of the compound in question was weighed into a 5 ml measuring flask. A small amount of acetonitrile was used to dissolve the substance. The flask was then filled up to the mark with the aqueous buffer. The precipitated compound was centrifuged and the clear supernatant was then tested for stability in solution for 24 hours at 37° C. The samples were evaluated using HPLC/UV. The results obtained for example I and C1 are shown in the table below:

| pH conditions | Example I Increase of the area of the impurities in percent | C1 Increase of the area of the impurities in percent |
| --- | --- | --- |
| pH 1.2 | 4.9 | 13.3 |
| pH 6.8 | 0 | 0.5 |
| pH 8.0 | 0.2 | 4.6 |

Thus, depending on the pH, the compound of the formula I according to the invention is at least 2.7 times more stable than C1 and, accordingly, forms fewer by-products than C1. Smaller amounts of by-products with systemic action mean a reduced potential for unwanted side-effects.

The invention claimed is:

1. A compound of formula I

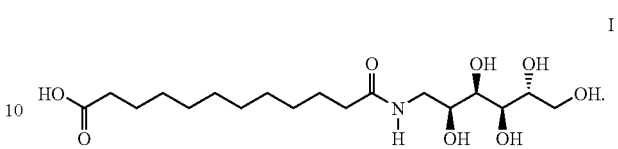

* * * * *